(12) United States Patent
Rubin et al.

(10) Patent No.: US 10,130,684 B2
(45) Date of Patent: Nov. 20, 2018

(54) ORAL DISSOLVING FILMS FOR INSULIN ADMINISTRATION, FOR TREATING DIABETES

(75) Inventors: Yoram Rubin, Haifa (IL); Smadar Cohen, Beer Sheva (IL); Eyal S. Ron, Lexington, MA (US)

(73) Assignee: PHARMEDICA LTD., Haifa (IL)

( * ) Notice: Subject to any disclaimer, the term of this patent is extended or adjusted under 35 U.S.C. 154(b) by 0 days.

(21) Appl. No.: 13/982,575

(22) PCT Filed: Jan. 30, 2012

(86) PCT No.: PCT/IL2012/000050
§ 371 (c)(1),
(2), (4) Date: Jul. 30, 2013

(87) PCT Pub. No.: WO2012/104834
PCT Pub. Date: Aug. 9, 2012

(65) Prior Publication Data
US 2013/0309294 A1 Nov. 21, 2013

Related U.S. Application Data

(60) Provisional application No. 61/438,987, filed on Feb. 3, 2011.

(51) Int. Cl.
*A61K 38/28* (2006.01)
*A61K 9/00* (2006.01)
*A61K 47/10* (2017.01)
*A61K 47/32* (2006.01)
*A61K 47/34* (2017.01)
*C07K 14/62* (2006.01)

(52) U.S. Cl.
CPC ............ *A61K 38/28* (2013.01); *A61K 9/006* (2013.01); *A61K 47/10* (2013.01); *A61K 47/32* (2013.01); *A61K 47/34* (2013.01); *C07K 14/62* (2013.01)

(58) Field of Classification Search
None
See application file for complete search history.

(56) References Cited

U.S. PATENT DOCUMENTS

| 4,713,243 | A | 12/1987 | Schiraldi |
| 5,504,188 | A | 4/1996 | Baker |
| 2002/0004065 | A1* | 1/2002 | Kanios ................. A61K 9/7061 424/449 |
| 2005/0019588 | A1* | 1/2005 | Berry ...................... B29C 39/18 428/424.8 |
| 2005/0124724 | A1 | 6/2005 | Burton |
| 2005/0147658 | A1* | 7/2005 | Tapolsky et al. ............. 424/448 |
| 2005/0196442 | A1* | 9/2005 | Huang .................. A61K 9/2031 424/468 |
| 2007/0207192 | A1* | 9/2007 | Holl ....................... A61K 9/006 424/449 |
| 2007/0281003 | A1* | 12/2007 | Fuisz ..................... A61K 9/006 424/443 |
| 2010/0298213 | A1* | 11/2010 | Schaffer ................. C07K 14/72 514/6.7 |
| 2011/0020312 | A1* | 1/2011 | Narain .................... A61K 31/00 424/94.5 |
| 2011/0268720 | A1* | 11/2011 | Gruber et al. ............... 424/94.6 |
| 2011/0280925 | A1* | 11/2011 | Tan ........................ A61K 9/006 424/443 |
| 2012/0301535 | A1* | 11/2012 | Williams et al. ............. 424/443 |

FOREIGN PATENT DOCUMENTS

| EP | 214826 | 3/1987 |
| EP | 368187 | 5/1990 |
| EP | 705275 | 4/1996 |
| EP | 792290 | 9/1997 |
| WO | 97/41097 | 11/1997 |
| WO | 97/41119 | 11/1997 |
| WO | 97/41120 | 11/1997 |
| WO | 98/08871 | 3/1998 |
| WO | 98/45292 | 10/1998 |
| WO | 99/19313 | 4/1999 |
| WO | 00/23415 | 4/2000 |
| WO | 00/23416 | 4/2000 |
| WO | 00/23417 | 4/2000 |
| WO | 00/23425 | 4/2000 |
| WO | 00/23445 | 4/2000 |
| WO | 00/23451 | 4/2000 |
| WO | 00/41121 | 7/2000 |
| WO | 00/50414 | 8/2000 |
| WO | 00/63153 | 10/2000 |
| WO | 00/63189 | 10/2000 |
| WO | 00/63190 | 10/2000 |
| WO | 00/63191 | 10/2000 |
| WO | 00/63192 | 10/2000 |
| WO | 00/63193 | 10/2000 |
| WO | 00/63196 | 10/2000 |
| WO | 00/63209 | 10/2000 |

OTHER PUBLICATIONS

Dey et al. "Preparation of carvedilol transdermal patches and the effect of propylene glycol on permeation" 2010.*

* cited by examiner

*Primary Examiner* — Robert A Wax
*Assistant Examiner* — Danah Al-Awadi
(74) *Attorney, Agent, or Firm* — Pearl Cohen Zedek Latzer Baratz LLP

(57) ABSTRACT

Provided are orally administrable thin film dosage forms adapted to adhere to a mucosal tissue of a patient, wherein said film comprises mixtures of polymers and insulin.

7 Claims, 4 Drawing Sheets

Back. Lay.

ORAL DISSOLVING FILMS FOR INSULIN ADMINISTRATION, FOR TREATING DIABETES

REFERENCE TO CO-PENDING APPLICATIONS

Priority is claimed as a 371 international of PCT/IL2012/000050, filed on Jan. 30, 2012; which further claims priority to U.S. provisional patent application Ser. No. 61/438,987, filed on Feb. 3, 2011.

FIELD OF THE INVENTION

The invention relates to oral film-shaped medicament formulations for administration of insulin, derivatives thereof, insulin analog, pre-insulin or prodrugs thereof, and to the use of said films for treating diabetic patients.

BACKGROUND OF THE INVENTION

All publications mentioned throughout this application are fully incorporated herein by reference, including all references cited therein.

Diabetes mellitus, hereinafter referred to as diabetes, represents a group of metabolic diseases in which high blood sugar is evident (hyperglycemia), either because the body does not produce enough insulin, or because cells do not respond to the insulin that is produced. This high blood sugar produces the classical symptoms of polyuria (frequent urination), polydipsia (increased thirst) and polyphagia (increased hunger), and if not treated may lead to various complications such as stroke, heart attack, kidney diseases and nerve damage.

Diabetes may be classified as Type 1 or Type 2 diabetes. Type 1 diabetes (juvenile diabetes), also referred to as insulin-dependent diabetes mellitus (IDDM), results from the body's failure to produce insulin. Type 2 diabetes, also referred to as non-insulin-dependent diabetes mellitus (NIDDM), results from insulin-resistance of the cells. Two other forms of diabetes include congenital diabetes, which results from genetic defects of insulin secretion, and gestational diabetes, which occur at about 5% of all pregnant women.

Diabetes without a proper treatment can cause many complications, e.g. hypoglycemia, diabetic ketoacidosis, nonketotic hyperosmolar coma, cardiovascular disease, chronic renal failure, and retinal damage. Adequate treatment of diabetes is thus important, as well as lifestyle factors such as smoking cessation and healthy diet regimen.

Insulin is a peptide hormone composed of 51 amino acids: an A chain of 21 amino acids linked by two disulfide (S—S) bridges to a B chain of 30 amino acids. It is produced in the islets of Langerhans in the pancreas, and is a central player in carbohydrate and fat metabolism regulation in the body. Insulin causes cells to take up glucose from the blood. When insulin is absent, glucose is not taken up by body cells and the body begins to use gluconeogenesis or fat as an energy source. In addition, it has several other anabolic effects throughout the body. Insulin also influences other body functions, such as vascular compliance and cognition. It was also found that enhancing brain insulin signaling by means of intranasal insulin administration also enhances the acute thermoregulatory and glucoregulatory response to food intake, suggesting that central nervous insulin contributes to the control of whole-body energy homeostasis in humans.

Since the discovery of insulin in 1921, Type 1 diabetes has been treatable by a simple administration of exogenous insulin, most commonly by subcutaneous injections. Type 2 diabetes patients are either insulin resistant, have relatively low insulin production, or both. While Type 2 diabetes has been controlled with medications and diet, certain patients with Type 2 diabetes may eventually require insulin if other medications fail to control blood glucose levels adequately. Several surgical attempts to treat diabetes, e.g. pancreas or beta cells transplants (for Type 1 diabetes), and gastric bypass surgery (for Type 2 diabetes), are expensive, complicated and insufficient. Therefore, it is an object of the invention to provide easy, painless and non-invasive administration of insulin for treating diabetes.

Nowadays, insulin cannot be taken orally. This is since when introduced into the gastrointestinal tract, the insulin is subjected to degradation from stomach acid, bile, digestive enzymes and other first pass effects. As a result, the insulin loses all of its activity. Attempts to produce insulin pills for oral administration have yet to succeed. Accordingly, insulin is administered mainly via subcutaneous injections by: a disposable syringe with a needle; an insulin pump; or a repeated-use insulin pen with a needle. Administration schedules attempt to mimic the physiologic secretion of insulin by the pancreas. Hence, both a long-acting insulin and a short-acting insulin are typically used.

Patients who wish to reduce repeated skin puncture of insulin injections often use an injection port in conjunction with syringes, or use insulin pumps. However, both techniques have disadvantages such as cost, the potential for hypoglycemic and hyperglycemic episodes, catheter problems, and no means of controlling insulin delivery based on current blood glucose levels. In addition, indwelling catheters pose the risk of infection and ulceration, and some patients may also develop lipodystrophy due to the infusion sets. In addition, insulin pumps require care and effort to use correctly.

Other administration means have been developed to administer insulin, such as inhalation, transdermal delivery, and intranasal administration, each with its own disadvantages and drawbacks.

Many researches have been conducted to find various methods of therapy for treating diabetes. Nevertheless, the current known methods suffer from one or more inadequacies. Thus, there remains a need for an improved method for administering insulin to treat diabetes. The present invention provides such a contribution to the art based on the finding that insulin can be administered via the oral mucosa by using thin films.

Accordingly, it is an object of the invention to provide a simple, cost efficient and easy to use, advantageous way to administer insulin, without puncturing the patient's skin, by using orally dissolving thin films.

Orally dissolving films, also referred to as mucoadhesive films, eroding thin films or oral bioadhesive films, provide a useful alternative to traditional tablets, capsules, soft gels, liquids and injections. These thin films contain active pharmaceutical ingredient(s), and are designed for intra-oral administration, with the patient placing the strip on or under the tongue (lingual or sublingual) or along the inside of the cheek (buccal). As the thin film dissolves/erodes, drug is released and delivered to the blood stream either intragastrically, buccally or sublingually.

There are two categories of orally dissolving films: fast dissolving films and slow dissolving/eroding ones. Fast dissolving films, usually comprising polymers of high water solubility, are typically designed for lingual administration and gastro-intestinal tract absorption. The active ingredients are incorporated in the film matrix, which rapidly dissolves and is then swallowed for absorption. Fast dissolving films are particularly useful for pediatric and geriatric patients, and for patients with difficulty in swallowing tablets. It is also known in the art to use such films for providing breath freshening agents or various medicaments for treating cold, cough, flu and anti-snoring. These films are generally comprised of a water-soluble polymer(s) suitable for human consumption and compound(s) that enhance the flexibility and wettability of the film, typically selected from polyols, surfactants and other plasticizers.

Slow dissolving films contain at least one slow dissolving or eroding polymer, and are designed for controlled or sustained release of the active agent, primarily for systemic administration via the interior lining of the cheek (buccal mucosa) or for local treatment. U.S. Pat. No. 4,713,243 describes an extruded thin film, useful in intra-oral controlled-releasing delivery.

Thus, it is a further aspect of the invention to provide orally dissolving films containing insulin for immediate- and/or sustained-release of insulin to a patient in need thereof.

Another object of the invention is to provide bioadhesive orally dissolving films containing insulin for improving onset of action, lowering the dosing, and enhancing the efficacy and safety profile thereof. Said films also improve the dosing accuracy relative to other administration forms. Notably, the films of the invention may dissolve rapidly without the need for water, which provides an easy alternative to patients with swallowing disorders and to patients suffering from nausea, such as after chemotherapy.

In yet another aspect of the invention, provided are orally dissolving bilayer films which combine the advantages of both fast- and slow-dissolving films. In another embodiment, the invention provides a single-layer film for immediate- and/or sustained-release of insulin. The films of the invention may further comprise one or more active agents such as tooth whitening materials, breath fresheners, anti-cavity compounds, additional anti-diabetic agents, taste masking agents, flavor agents, etc., which may be delivered to the oral cavity. Both film types provide for ease of application.

An additional aspect of the invention is to provide orally dissolving single-layer films which comprise short-acting forms of insulin (such as lispro, aspart and glulisine) as well as long-acting forms of insulin (such as Neutral Protamine Hagedorn (NPH)/isophane, lente, ultralente, glargine, and detemir), thereby achieving immediate- and prolong-effect.

The films of the invention may comprise additional flavor agents, flavor masking agents, and colorants.

Another aspect of the invention is the method of insulin administration. In certain embodiments, the insulin-containing film is applied to the tongue and adheres to the palate. The film is designed to be flexible and bioadhesive. The film is also designed such that it disintegrates and dissolves upon administration and the drug is released for oral and/or transmucosal absorption. In addition, the films of the invention provide a method to alleviate or eliminate undesired taste or sensation of insulin.

These and other objects and advantages of invention will become apparent as the description proceeds.

SUMMARY OF THE INVENTION

It has now been found that insulin can be administered by using orally dissolving films, thus treating diabetic patients. Although Diabetic patients have been treated with insulin ever since it was discovered in 1921, this invention is the first to demonstrate insulin administration via absorption through the oral mucosa by applying thin films thereto.

The invention relates to a thin film for delivering and releasing insulin, or an acceptable active agent thereof via absorption through the oral mucosa. According to certain embodiments, the oral film contains insulin for delivery and release into the oral cavity of an individual so that it is absorbed through the oral mucosa and directly enters the individual's systemic circulation.

The invention provides a consumable thin film dosage form adapted to adhere to a mucosal tissue of a patient, wherein said film comprises an active agent, and at least one of the following compositions: a first polymer composition comprising water-soluble polymer(s), which enables the dissolution and immediate release of the active agent within 20 minutes or less; and a second polymer composition comprising hydrophilic, bioadhesive polymer(s), which enables the continuous release of the active agent for a time period of from about 1 h to about 24 hours, wherein the dosage form has a thickness of about 0.5 mm or less, and wherein the active agent is selected from insulin or insulin analog, or mixtures thereof.

The films of the invention will generally contain, polymers, active agent(s), taste modifiers, plasticizers and or release modifiers, buffering agents, preservatives or stabilizers, and the like.

The thin film dosage form may be a single-layer, double-layer, or multi-layer mucoadhesive film, which comprises at least one water soluble film forming polymer and an effective amount of insulin, a pharmaceutically acceptable analog thereof, or a combination thereof.

According to certain embodiments, said oral thin film comprises:
  about 5 to about 20 wt % permeation enhancer(s) (e.g. Brij 58, Brij 35, and sodium glycocholate);
  about 1 to about 10 wt % flavorant(s) (e.g. peppermint oil, strawberry flavor, and saccharin);
  about 0.5 to about 10 wt % insulin or insulin analog;
  about 0.01 to about 1 wt % chelating agent (e.g. EDTA, Versene NA);
  about 10 to about 30 wt % plasticizer (e.g. PEG400); and
  about 40 to about 90 wt % water soluble and hydrophilic polymers (e.g. Kollicoat IR and Carbopol 971), and optionally
  one or more colorants (e.g. FD&C Red No. 40).
(percentages are Dry percentages).

A method of delivering an active agent to a patient, comprising applying the thin film dosage form of the invention to a mucosal tissue, is also disclosed herein. Said mucosal tissue may be in the mouth, especially buccal mucosa, palate mucosa or the sublingual mucosa.

A method of using a slow disintegrating oral film to administer an effective amount of insulin to the oral cavity is further provided.

In one aspect of the invention, insulin is used in the manufacture of the thin film dosage form of the invention for treating diabetes. Also provided is a method of treating diabetes, comprising orally administering the insulin-containing film of the invention.

These and other aspects of the invention will become apparent by the hand of the following figures.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The above and other characteristics and advantages of the invention will be more readily apparent through the following examples, and with reference to the appended drawings, wherein:

FIG. 2. shows results of an exemplary experimental insulin film of the invention.

Abbreviations: Ad. Lay. (Adhesive layer), Back. Lay. (Backing layer).

Figure 3A:
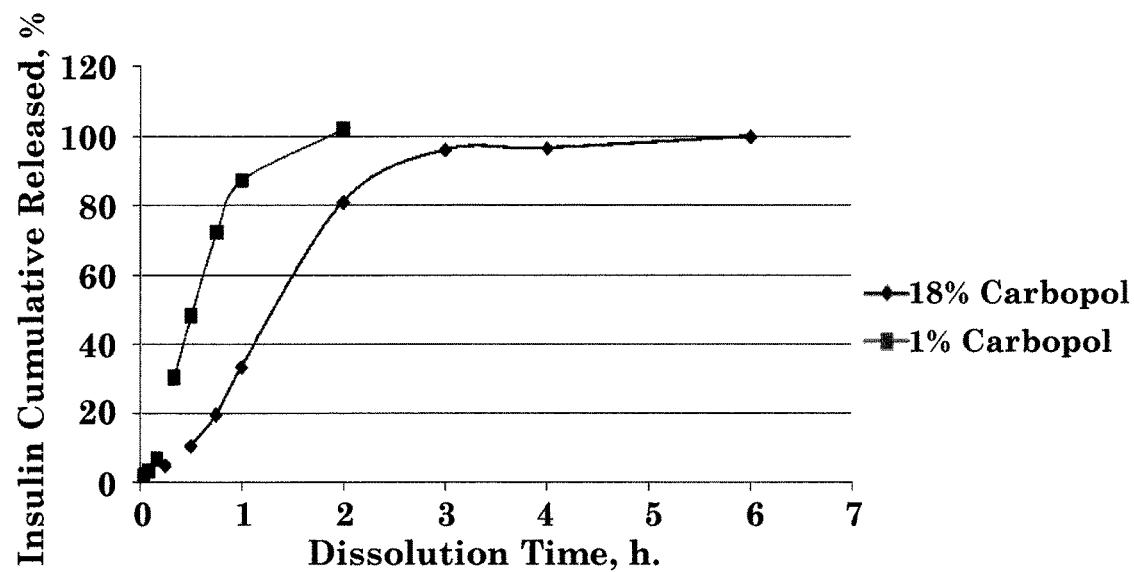
Figure 3B:
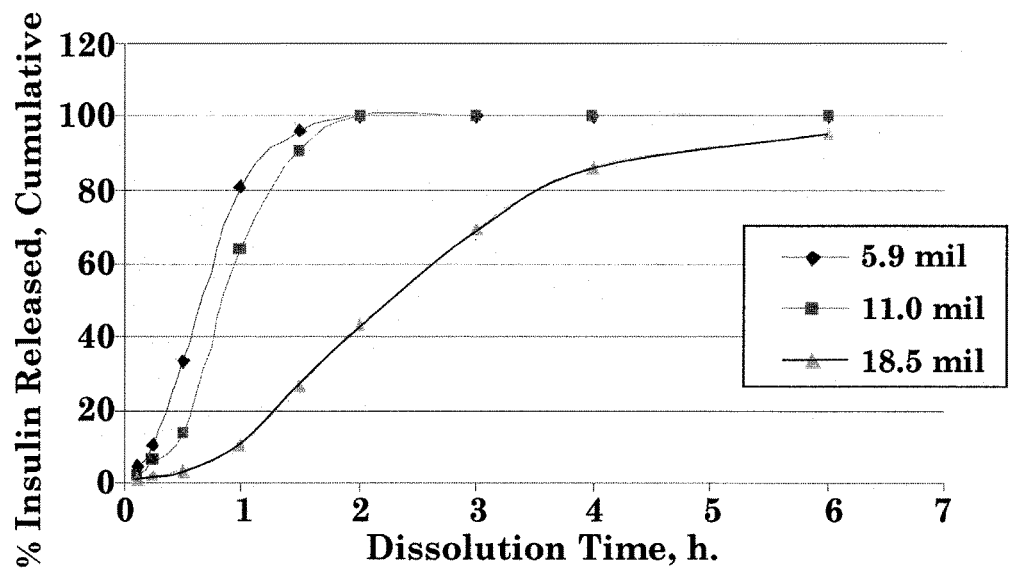

FIG. 3. demonstrates film thickness results. FIG. 3a is a graph comparing different Carbopol content; and FIG. 3b is a graph comparing three different film thickness.

Figure 4:
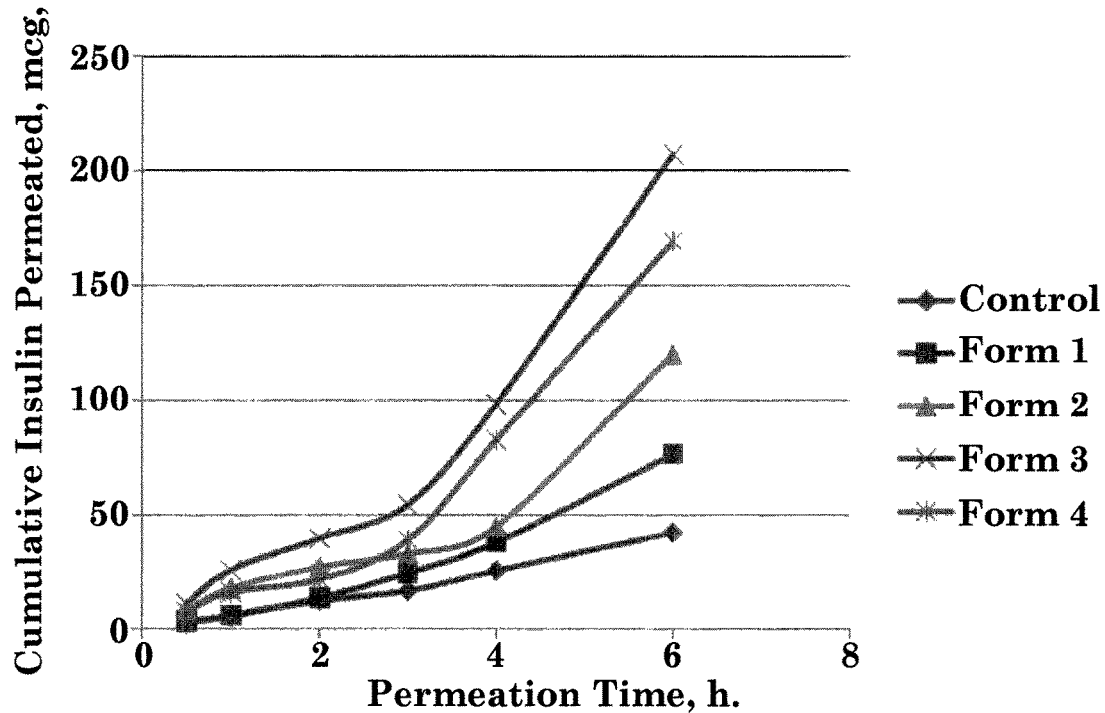

FIG. 4. is a graph showing insulin absorption as a dependency of permeation enhancers content.

Figure 5:
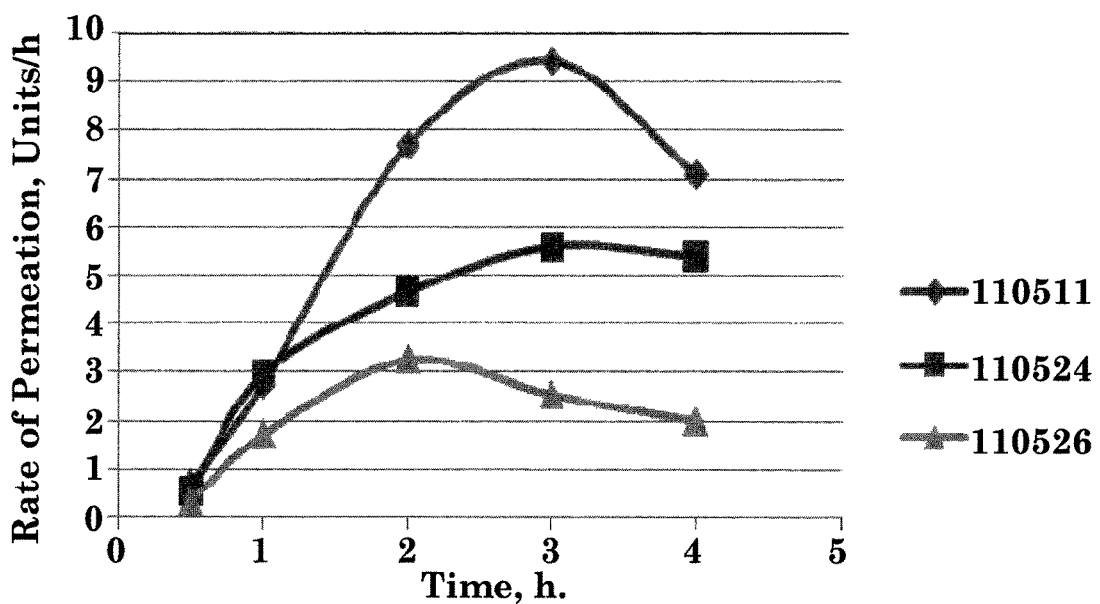

FIG. 5. is a graph showing insulin permeation of films of the invention.

DETAILED DESCRIPTION OF THE INVENTION

Oral administration of insulin through any conventional administration form such as tablets, capsules, suspensions or solutions is not possible due to the degradation of insulin in the gastrointestinal tract. Known means for insulin administration are disadvantageous insofar as they are costly or require invasive means, such as injections.

The object of the present invention is therefore to provide novel insulin administration forms, which are suitable for treating diabetic patients, while avoiding all of the disadvantages of the known techniques, as far as possible. It has surprisingly found out that this objective is achieved by oral thin-film-shaped dosage forms containing insulin.

The film-shaped film of the invention may comprise at least one polymer-containing layer which serves as an active substance reservoir and which contains the insulin and is able to release it upon the action of saliva. The polymer portion of this polymer-containing layer amounts from 40 to 90% wt, preferably from 45 to 80% wt. and particularly preferably from 50 to 70% wt.

In the simplest case, the inventive preparation only consists of a single, active substance-containing layer, which is designed for immediate-release or sustained-release of insulin, or a combination of both. However, the invention also encompasses embodiments with a two-, three- or multilayer structure of which at least one layer contains insulin. The various layers may differ from one another in terms of their active substance content (type, concentration, biological activity, release rate, etc.), their mucoadhesive properties, disintegration properties, solubility, etc.

The term "film-shaped" means that the inventive medicaments, unlike conventional tablets, are of small thickness and are preferably bendable. Furthermore, after having absorbed moisture they are generally capable of conforming to the irregular surface contour of the mucosa. The total typical thickness of the films (prior to application) is from 0.05 to 3 mm, preferably up to 2 mm, more preferably, up to 1 mm.

It is advantageous that the insulin can be administered in a simple, inconspicuous and safe manner, since film-shaped preparations of small thickness, e.g. less than 0.5 mm, are felt to be pleasant by the patient.

The oral dosage films (single- or multi-layer) can be in any shape or form (such as square, rectangular, circular, oval, etc.). The film is typically from 30 mil (0.762 mm) to 4 mil (0.101 mm) in thickness. Many different sizes can be employed. Illustrative film areas (e.g., length×width) include 25 $cm^2$ or less and 5 $cm^2$ or more. Illustrative film weights include from 5 mg to 20 mg.

The oral film-shaped of the invention surprisingly enables transmucosal absorption of insulin (and/or analog thereof) in the region of the oral mucosa. The films may be applied buccally, palately, or sublingually. The inventive films avoid the first-pass metabolism and enable a rapid onset of action (within approximately 5 sec. to 30 min.). The films of the invention are applied in the oral cavity, whereupon the insulin is released therefrom as a result of the action of saliva, and subsequently absorbed via the oral mucosa. The invention also encompasses mucoadhesive film-shaped preparations which are applied to the oral mucosa and remain adhered thereto. Thus, enable delivery of the insulin directly via the mucosal region of the application site, where the film-shaped preparation is in direct contact with the oral mucosa.

An oral film for delivering and releasing an active agent, preferably insulin and/or analog thereof, into the oral cavity is provided. The composition of the oral film provides a mucoadhesive film having a delayed or slow disintegration and release of active agent(s) from the film. The rate of disintegration of the film and release of the active agent(s) from the film within the conditions of the oral cavity maximizes the absorption of said active agent(s) through the oral mucosa.

According to certain embodiments, the oral film comprises at least one water soluble film forming polymer and insulin. The term "insulin" refers to all forms of insulin, insulin derivatives, insulin salts, and salts of insulin derivatives, insulin analog, salts of insulin analog, insulin complexes, and combinations or mixtures thereof. A variety of insulin active forms are well known in the art and are commercially available.

It is noted that "insulin" as used herein, includes native insulin, pre-insulin, insulin prodrugs, insulin analog, insulin derivatives, recombinant insulin or insulin from any origin, or any acceptable form thereof which have activity similar to native insulin.

The invention also encompasses insulin prodrugs, which on administration undergo chemical conversion by metabolic processes before becoming pharmacologically active substances. In general, such prodrugs will be functional derivatives of present compounds, which are readily convertible in vivo into active insulin.

In a further aspect of the invention, the oral film may contain additional active agents to be released into the oral cavity. An "active agent" includes cosmetically or pharmacologically active agents, such as tooth whitening materials, tooth desensitizing agents, breath fresheners, anti-cavity compounds, anti-anxiety, anti-oxidants, anti-convulsants, additional anti-diabetic agents, anti-epileptic agents, anti-inflammatory agents, anti-psychotic agents, analgesics, anti-histamines, local anesthetics, anti-bacterial compounds, disinfectants, vasoconstrictors, vasodilators, hemostatics, chemotherapeutics, antibiotics, anti-fungals, anti-hypertensives, anti-migraine, anti-arrhythmics, anti asthmatics, cardiac agents, calcium antagonists, cold remedies, cough remedies, nicotine, peptides or prodrugs, hormones, proton pump inhibitors, H2 receptor antagonists, vitamins and other dietary and nutritional supplements. The above list of active agents is merely provided to illustrate the types of active agents which may be incorporated into the oral film. It should be noted, however, that any other compatible cosmetically or pharmacologically active agent or a combination of agents may be included in the oral film.

The present invention relates to a consumable thin film dosage form adapted to adhere to a mucosal tissue of a patient, wherein said film comprises an active agent, and at least one of the following mixtures: a first mixture of polymers, comprising predominantly of highly water-soluble polymer(s), which enables dissolution and immediate release of the active agent within 20 minutes or less; and a second mixture of polymers, comprising predominantly of hydrophilic, bioadhesive polymer(s), which enables continuous release of the active agent for a time period of from about 1 h to about 24 hours, wherein the dosage form has a thickness of about 0.5 mm or less, and wherein the active agent is selected from insulin or insulin analog, or mixtures thereof.

The thin film dosage form is applied to the oral cavity and adheres to a mucosal surface, such as the cheek, or palate, where the film disintegrates and releases the insulin for absorption through the oral mucosa. The oral film has a high mucoadhesivity to the oral mucosa and slow disintegration rate, which enable the insulin to be absorbed substantially at the point of adhesion within the oral cavity, thus minimizing the amount of swallowed insulin. The release of insulin from the thin film occurs without mastication, such as chewing or sucking of the film, and there is no risk of choking or swallowing the whole dosage form, which may occur with tablets, capsules or lozenges. The composition of the oral film start dissolving quickly in the oral cavity. In some embodiments the composition may start dissolving as quickly as about 30 seconds, and may still remain active in some films for up to about 24 h.

According to one embodiment of the invention, the oral film-shaped of the invention is characterized in that at least 10% insulin is released therefrom and adsorbed in the systemic circulation. More specifically, at least 15% insulin is released from the film and adsorbed in the systemic circulation. Even more specifically, at least 20% insulin is released from the film and adsorbed in the systemic circulation.

Although oral, especially buccal, palate or sublingual, administration is preferred, the invention also encompasses administration forms which are intended for application to other mucosal surfaces, such as rectal, vaginal or intranasal areas of the human or animal body, and which enable the transmucosal administration of insulin.

In an embodiment of the invention the thin film dosage form is a single-layer flexible thin film dosage form.

In another embodiment of the invention the thin film dosage form is a dual-layer flexible thin film dosage form, which comprises: one side comprising the active agent(s), which adheres to the, e.g. buccal tissue; and a second side without the active agent, which acts as a blocking layer providing unidirectional absorption of the active agent to the tissue and preventing drug diffusion to the opposite direction. Preferably, each layer has a different color.

In another embodiment of the invention the thin film dosage form is a dual-layer flexible thin film dosage form, which comprises: a quick-release side comprising a mixture of polymers, which comprises predominantly of highly water-soluble polymer(s), and an active agent, wherein the mixture enables immediate release of the active agent within 20 minutes or less; and a sustained-release side comprising a mixture of polymers, which comprises predominantly of hydrophilic, bioadhesive polymer(s), and a second active agent, which can be the same or different from the first active agent, wherein the mixture enables a continuous release of the active agent for a time period of from 1 h to about 24 hours, wherein the dosage form has a thickness of about 0.5 mm or less, and wherein both active agents are selected from insulin or insulin analog, or mixtures thereof. According to a specific embodiment the sustained-release side is laminated.

It is understood that the thin film dosage form of the invention is suitable for transmucosal, especially buccal, administration of the active agent(s) contained therein. According to one embodiment, the thin film dosage form of the invention is characterized in that it is mucoadhesive or has at least one mucoadhesive outer surface.

In another embodiment the thin film dosage form of the invention is characterized in that it has a three- or multi-layer structure, with at least one layer containing an active agent selected from insulin or insulin analog, or mixtures thereof. Said each layer may have a distinct color.

In an embodiment of the invention, the release of the active agent in the thin film dosage form begins within 15 min. of administration, preferably within 10 min. In yet another aspect of the invention, the active agent is continuously released for a time period of from 3 h to 24 h, preferably up to 12 h.

According to one embodiment of the invention, the thin film dosage form is characterized by the fact that following application they release the insulin contained therein into the oral cavity, in such an amount that an effective plasma level is achieved for the desired time. Typical desired times may vary in the range of 24 h to 3 h after application, but longer or shorter rimes are possible.

In another aspect, the thin film dosage form of the invention is characterized in that the active agent(s) content is from 0.5 to 10% wt.

According to certain embodiments, the amount of the insulin included in the oral film of the invention is from about 0.25 to about 20 units per dose unit. According to another embodiment of the invention, overall insulin content of a film-shaped preparation according to the invention is from 3% or more, and up to 10% or less, preferably 5% or less. The insulin dose contained in a single film is in the range of from 0.1 to 3 mg. (Unless otherwise specified, the amounts or percentages in this specification are w/w amounts or percentages).

The content of the plasticizer may vary. Illustrative contents may be from 15% to 40%. Plasticizers suitable for use in the film of the invention will be recognized by those of skill in the art, and may include, e.g., propylene glycol, glycerin, PEG-4000, PEG-400, and the like. The desired plasticizer can also have surfactant properties, so that it acts as a release modifier, e.g. non-ionic detergents such as Brij 35 (polyoxyethylene (35) lauryl ether), Brij 58 (polyoxyethylene (20) acetyl ether), and the like. Plasticizers impart flexibility to the dosage forms, and can affect the release profile of the active agent(s) therein.

Another feature of the invention is a thin film dosage form, wherein the highly water-soluble polymers is selected from the group consisting of cellulose, cellulose derivatives, polyethylene oxide, polyalkylene oxides, polyalkylene glycols, synthetically or naturally occurring gums, acrylic acid polymers, acrylic acid copolymers, methacrylic acid polymers, methacrylic acid copolymers, polyacrylamides, carrageanan, pullunan, polyvinyl pyrrolidone, polyvinyl alcohol, alginic acid, polyethylene glycol-polyvinyl alcohol copolymers, salts of alginic acid, carboxyvinyl polymers, and mixtures thereof. In yet another feature, said highly water-soluble polymers is selected from the group consisting of pullulan, sodium alginate, polyacrylic acid, methylmethacrylate copolymer, amylose, high amylose starch, hydroxypropylated high amylose starch, dextrin, pectin, chitin, chitosan, levan, elsinan, collagen, gelatin, zein, gluten, soy protein isolate, whey protein isolate, casein and mixtures thereof.

In the sustained-release part of the film of the invention, the hydrophilic, bioadhesive polymer can likewise in certain embodiments be present in an amount of from 15% to 40%. The highly water-soluble polymer can in certain embodiments be present in an amount of from 25% to 40%.

In the immediate-release part of the film of the invention, the hydrophilic, bioadhesive polymer can in certain embodiments be present in an amount of from 1% to 30%. The highly water-soluble polymer can in certain embodiments be present in an amount of from 20% to 55%.

The hydrophilic, bioadhesive polymers used in the films of the invention may be selected from natural polymers, modified natural polymers, and synthetic polymers. Examples for such polymers are xanthan gum, carrageenan, pectin, sodium carboxymethylcellulose, alginate, polyacrylic acids, high molecular weight polyethylene oxide, or mixtures thereof. In some embodiments, predominantly hydrophilic, bioadhesive polymers comprise polyacrylic acids, high molecular weight polyethylene oxide, or mixtures thereof. Such polyacrylic acids include, for example, Polycarbophil polyacrylic acids and Carbopol, Carbopols are polymers of acrylic acid cross-linked with polyalkenyl ethers or divinyl glycol. Examples of such carbopols are, Carbopol 971, Carbopol 974. and Carbopol 1342.

Water soluble film forming polymers that are suitable for use in the present invention include, but are not limited to, cellulose, cellulose derivatives, polyalkylene oxides, polyalkylene glycols, synthetically or naturally occurring gums, acrylic acid polymers, acrylic acid copolymers, methacrylic acid polymers, methacrylic acid copolymers, polyacrylamides, carrageanan, pullunan, polyvinyl pyrrolidone, polyvinyl alcohol, alginic acid, polyethylene glycol-polyvinyl alcohol copolymers (Kollicoato IR, BASF), salts of alginic acid, carboxyvinyl polymers, and mixtures thereof.

Suitable cellulose derivatives include alkyl celluloses, such as methyl cellulose and ethyl cellulose, substituted alkyl celluloses, such as hydroxyethyl cellulose, hydroxypropyl cellulose, hydroxypropyl methylcellulose, carboxymethyl cellulose, salts of substituted alkyl celluloses, such as sodium carboxymethyl cellulose, and mixtures thereof. Suitable gums include xanthan gum, tragacanth gum, guar gum, acacia gum, arabic gum, and mixtures thereof.

The films of the invention might contain additional polymers not disclosed herein.

Additional details on polymers mentioned above can be found in Handbook of Pharmaceutical Excipients (Rowe et al., 2003, Handbook of Pharmaceutical Excipients. 4$^{th}$ Ed. Pharmaceutical Press, London).

The oral films of the invention may further contain at least one of taste modifying agents, bioadhesive agents, buffering agents, coloring agents, stabilizing agents, inert fillers, emulsifying agents, permeation enhancers, pH adjusting agents, plasticizers, and preservatives. Suitable taste modifying agents include, but are not limited to, flavorants, sweeteners, taste-masking agents, essential oils or water soluble extracts of e.g. menthol, and mixtures thereof. Said taste modifiers can be incorporated in the dosage form to provide a pleasant taste and mouth-feel when the dosage form is administered in the oral cavity.

The film of the invention may comprise at least one additional antidiabetic agent, such as those disclosed in EP 792 290 ($N^{\epsilon B29}$-tetradecanoyl des (B30) human insulin), EP 214 826 and EP 705 275 ($Asp^{B28}$ human insulin), U.S. Pat. No. 5,504,188 ($Lys^{B28}$ $Pro^{B29}$ human insulin), EP 368 187 (Lantus®), WO 98/08871 (GLP-1 and GLP-1 derivatives), all of which is incorporated herein by reference. Antidiabetic agents also refer to hypoglycemic agents, such as imidazolines, sulphonylureas (e.g. glibenclamide, glipizide, tolbautamide, chloropamidem, tolazamide, glimepride, glicazide and glyburide), biguanides, meglitinides, oxadiazolidinediones, thiazolidinediones (e.g. troglitazone, ciglitazone, piolitazone, rosiglitazone, isaglitazone, darglitazone, englitazone, CS-011/CI-1037 or T 174 or the compounds disclosed in WO 97/41097, WO 97/41119, WO 97/41120, WO 00/41121 and WO 98/45292, which are incorporated herein by reference), insulin sensitizers (e.g. GI262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193, WO 00/23425, WO 00/23415, WO 00/23451, WO 00/23445, WO 00/23417, WO 00/23416, WO 00/63153, WO 63196, WO 00/63209, WO 00/63190 and WO 00/63189, which are incorporated herein by reference), insulin secretagogues (e.g. glimepiride), α-glucosidase inhibitors (e.g. voglibose, emiglitate, miglitol or acarbose), and agents acting on the ATP-dependent potassium channel of the β-cells.

In still another embodiment of the invention the present films further comprise compounds lowering food intake, antiobesity agents, appetite regulating agents and/or antihypertensive agents.

The oral films may also optionally include one or more "permeation enhancers", which are natural or synthetic compounds that facilitates the absorption of an active agent through a mucosal surface.

The immediate-release section of the films of the invention is adapted to provide 20 min or less erodibility. In certain embodiments, the polymers and other components of the immediate-release section are adapted to provide 10 min or less erodibility. The sustained-release section of the films of the invention is adapted to provide up to 48 h erodibility. In some embodiments, the polymers and other components of the sustained-release section of the film are adapted to provide up to 24 h erodibility. In other embodiments, they provide up to 12 h or up to 3 h erodibility.

It is another object of the invention to include a pharmaceutically acceptable distinct dye to each layer of the multilayered film. The color can be used to inform the user of the preferred side for application to the tongue, such that the other side transfers to the palate.

A method for preparing a slow disintegrating oral film from at least one water soluble film forming polymer and insulin is provided.

Production of the film of the invention can be done in any known method such as solvent-casting method, hot-melt extrusion process, or as solidified foams. The produced thin-film can be packaged e.g. individually in single pouches as single unit doses.

According to a certain embodiment, the method for preparing the oral thin film comprises: mixing at least one water soluble film former and at least one stabilizing agent to provide a film-forming mixture; dissolving water-soluble ingredients in water to provide an aqueous solution; combining said film-forming mixture and said aqueous solution to provide a hydrated polymer gel; casting the uniform gel on a substrate; and drying the cast gel to provide said film.

The inventive films may be used advantageously for treating diabetes or symptoms caused therefrom. The films of the invention may be used to treat persons (or animals) suffering from diabetes (of any type), wherein the patient is orally administered a therapeutically active dose of insulin in the form of a film-shaped medicament, as described herein.

The thin film is, in another aspect of the invention, advantageously used for treating all diabetes types, e.g. Type I, Type II, congenital diabetes, and gestational diabetes. Said treating may lead to disappearance or mitigation of all or part of the symptoms associated to diabetes.

To this end, the film-shaped preparation is introduced into the oral cavity (e.g. buccally, sublingually) and adhered to the buccal mucosa. Other regions of the oral mucosa (e.g. palate, gingival) are also suitable as application sites. Application is repeated as often as required, e.g. every 3 h, 12 h, or 24 h.

According to one embodiment of the method of the invention, the film is applied to the top of the tongue, and is then applied by transfer from the tongue to the palate.

In a specific embodiment, the thin film dosage form of the invention is stable for at least one month to one year, and may additionally contain at least one further pharmaceutically active substance which is not insulin. The term "stable" as used herein means that the active ingredients in the films maintain their biological activity. In some embodiments, the thin film of the invention is stable for at least one week to one month, one month to six months, or six months to one year.

In specific embodiments, the film of the invention is stable at 4° C. as well as at room temperature, said temperature ranging from about 10° C. to about 45° C.

According to further embodiments, the oral film maintains at least partial integrity and active agent(s) release capability after in vitro exposure to artificial human saliva solution for at least 3 h and, in some cases, up to 24 h. In another embodiment of the invention, the oral film maintains at least partial integrity and active agent(s) release capability after in vivo exposure to human saliva for at least 3 h and, in some cases, up to 24 h.

In one embodiment, the oral film maintains at least partial integrity and active agent(s) release capability for at least 12 h.

To term "effective amount" of an active agent includes an amount effective to treat, reduce, alleviate, ameliorate, eliminate or prevent one or more symptoms of the disease sought to be treated or the condition sought to be avoided or treated, or to otherwise produce a clinically recognizable favorable change in the pathology of the disease or condition. Active agents can be presented in the dosage form in effective amounts, or in a number of the dosage forms applied at about the same time in amounts that total effective amounts.

The term "patient" includes human and non-human animals. The patient to be treated is preferably a mammal.

The terms "treatment", "treating" and "treat", as used herein, include their generally accepted meanings, i.e., the management and care of a patient for the purpose of preventing, prohibiting, restraining, alleviating, ameliorating, slowing, stopping, delaying, or reversing the progression or severity of a disease, disorder, or pathological condition, described herein, including the alleviation or relief of symptoms or complications, or the cure or elimination of the disease, disorder, or condition.

The following examples are set forth to further illustrate the oral films of the invention. The below examples, however, should not be construed as limiting the present invention in any manner.

EXAMPLES

Example 1

HPLC Method

A HPLC assay method has been developed for determining insulin content in the film formulations of the invention, and for determining insulin concentration of the drug release medium and permeation study medium.

Equipment:
 Agilent 1100 HPLC equipped with a UV or DAD detector
 Agilent ChemStation Data Acquisition system Chemicals and Reagents:
 Insulin
 Acetonitrile (HPLC grade)
 Sodium Sulfate (HPLC grade)
 Hydrochloric Acid (Analytical or HPLC Grade)
 Phosphoric Acid (85% Analytical or HPLC grade)
 Deionized water
 Ethanolamine (Analytical or HPLC grade)

Chromatographic Conditions:
 Column: Zorbax C18 150 or 250×4.6 mm, 5 um or equivalent.
 Mobile Phase: 20 mmol sodium sulphate (PH=2.3): Acetonitrile.
 Flow Rate: 1 ml/min.
 Wavelength: 214 nm.
 Injection Volume: 200.
 Column Temperature: 40 degree.
 Retention Time: about 5 min.

Procedure:
a) Solution Preparation:
 Mobile Phase A: Prepared as described in USP method, 28.4 g sodium sulphate dissolved in 1000 ml of deionized water with 2.7 ml of phosphoric acid, PH modified with enthanolamine to PH 2.3. Mix, filter and degas prior to use.
 Mobile Phase B: In a 2 L clean container, add 2000 ml of acetonotrile. Filter and degas prior to use.
 Insulin diluent (0.01M HCl solution): In a 2 L clean volumetric flask, dissolve 1.0 ml 12N hydrochloric Acid in a 1200 ml of deionized water. Mix.
 Note: Volume of solutions may be scaled up or down, as needed.
b) Standard Preparation:
 Stock Standard Solution Preparation (~100 µg/ml): Accurately weigh approximately 10 mg insulin into a 100 ml volumetric flask and bring to the volume with insulin diluent. Record the exact weight. Calculate the concentration of stock solution in µg/ml (about 100 µg/ml)
 Working Standard Solutions Preparation: Seven working standard solutions at the concentrations of 0.5, 1, 5, 10, 25, 50, 75 µg/ml in 0.01M HCl are prepared from stock standard solution.

Quality Control Solutions Preparation: three quality control (QC) samples at the concentrations of 7.5, 20 and 40 µg/ml in 0.01M HCl are prepared from the stock standard solution.

c) System suitability:

The system suitability is assessed by six replicate analyses of human insulin at a concentration of 25 µg/ml. Calculate the percent relative standard deviation (% RSD) for the peak area and retention times for human insulin.

d) Linearity:

Standard solutions containing 0.5-100 µg/ml of insulin are prepared and 20 µl injected into HPLC.

e) Accuracy and Precision: Accuracy of the assay method is determined for both intra-day and inter-day variations using the six times analysis of the QC samples. Repeatability (3 control samples, 6 times/each) and Intermediate precision (3 control samples, 6 times/each 3 days).

f) Sensitivity (LOD and LOQ): LOD (S/N=3), LOQ (S/N=10)

g) Recovery:

The recovery is checked as three different concentration levels (3, 25, 45 µg/ml) and analytical recovery experiments is performed by adding known amount of pure drugs to placebo solution or pre-analyzed samples. Six replicate determinations/each.

h) Stability: Stability studies indicate that the samples are stable when kept at room temperature and at refrigerated temperature for 24 h and 48 h.

Drug dissolution tests, were conducted by placing the film (a 2.3 cm×2.3 cm unit dose) in an agitated (at 100 rpm) bottle containing 100 mL USP phosphate buffer (pH 6.8) at 37° C. Typically, samples were withdrawn at 5 min, 15 min, 30 min, 1 h, 1.5 h, 2 h, 3 h, 6 h and 12 h for HPLC assay for insulin.

Example 2

BXN-104 Insulin Orally Dissolving Film (ODF)

As a first step, an HPLC method was developed according to Example 1 above.

Subsequently, fast dissolving layer (FDL) thin films were prepared, comprising:

| Ingredient | Manufacturer | Wet g, Actual | Dry g | Dry % |
|---|---|---|---|---|
| Brij 58 | Croda | 1.42 | 1.42 | 13.4% |
| Peppermint oil american USP | AM Todd | 0.32 | 0.32 | 3.0% |
| Art Strawberry Flavor | | 0.13 | 0.13 | 1.2% |
| Carbopol 971P, 2% | Noveon | 5.63 | 0.11 | 1.1% |
| Insulin | Spectrum | 0.457 | 0.46 | 4.3% |
| Sodium EDTA | Versene NA | 0.05 | 0.05 | 0.5% |
| Water | Lab | 27.15 | | |
| PEG400 | Dow | 2.57 | 2.57 | 24.3% |
| Kollicoat IR | BASF | 5.29 | 5.29 | 50.1% |
| Syncal GS (Sacharrin) | PMC | 0.21 | 0.21 | 2.0% |
| FD&C Red | | 0.00 | | |
| Total | | 43.23 | 10.56 | |

Film Fabrication Method:

The solvent-casting method was used for fabricating thin polymeric matrix films. However, other techniques can also be used. The general solvent-casting fabrication process consists of:

1. Preparing Wet Casting Solution:

Mixing the active ingredient with the polymers, plasticizers, buffering agents, etc. in an aqueous and/or alcoholic solution to form a homogenous casting solution with a solid content of 20-40% and a viscosity of 5,000-20,000 cP.

2. Casting of Wet Film:

Uniformly coating the homogenous coating solution onto a casting polyester release liner with predetermined thickness (20-50 mil wet film thickness).

3. Drying of the Film:

Drying the cast film in a forced-air oven at 60-80° C.

4. Die-Cutting of the Film:

Die-cutting the dried film into desired shape and sizes (e.g. squares of 2.3 cm×2.3 cm) of dosage units (individual unit-dose squares).

5. De-Lamination of Thin-Film Units:

De-lamination of die-cut squares from the liners, and removal and discarding of casting release liners.

6. Pouching of Finished Discs:

Pouching of the de-laminated dosage discs by sealing pre-cut pouching stock material. The final thin-film discs are individually packaged in single pouches as single unit doses.

Preparation Procedures.

The procedure is divided into two parts: oil phase, and aqueous phase preparations.

Oil Phase Preparation

1. In a beaker, weigh in the liquid components, i.e. PEG 400 and peppermint oil.
2. Add in ethanol (solvent) and dissolve content in 1.
3. Weigh Carbopol in a weighing pan, gradually add to 2, while mixing.
4. Mix for 20 to 30 min. to obtain smooth, homogeneous paste dispersion.

Aqueous Phase Preparation

5. In a beaker, weigh in EDTA, Brij 58 and Syncal GS.
6. Add in water while mixing. Mix till all solids are dissolved.
7. Weigh Kollicoat in a weighing paper, add in while mixing. Continue mixing until dissolve.
8. Weigh and add in insulin while mixing. Mix for about 15 min.
9. Add 8 to 4. Mix till homogeneous. It may take up to 2 h.
10. Coat 50 wet mils (or higher for thicker films) using casting applicator on polyester release side.
11. Dry the coating from Step 8, in a forced air oven at 65° C. for 30 min.
12. Die-cut into 2.3 cm×2.3 cm round-cornered squares.
13. Pouch the films.

Each film is 2.3 cm×2.3 cm, weighs about 100 mg. Each film has adequate structural integrity and flexibility. Each film has 4.3% (theoretical value) insulin. HPLC assay showed that each film has 4.5 mg insulin.

Figure 1:
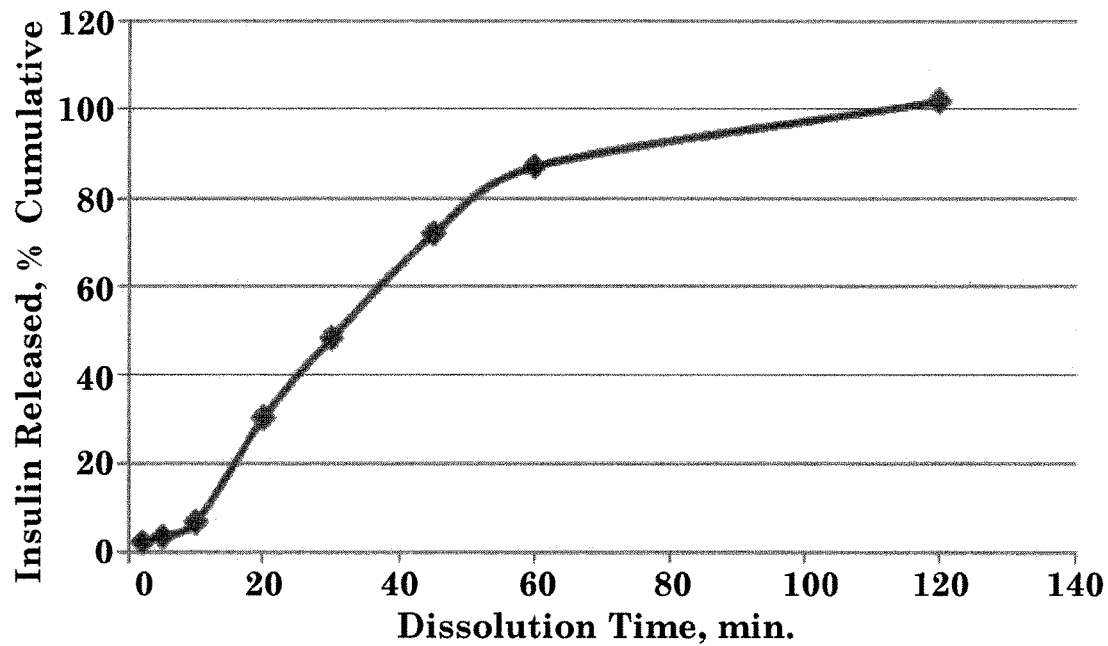
FIG. 1. shows graphic results of insulin release data.

Insulin release from the films into the medium was analyzed. The results, as demonstrated in FIG. 1, show that in FDL films, almost 50% of the insulin is released after 30 minutes, and that most of the insulin is released within 2 hours after application.

Similar films were prepared with Brij 35 or sodium glycocholate as permeation enhancers for insulin, instead of Brij 58.

Example 3

BNX-104 Insulin ODF, 450 Units

Figure 2A:
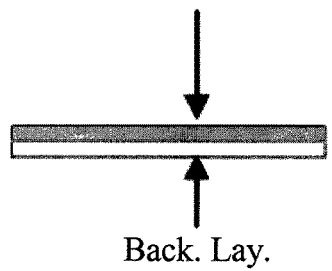
FIG. 2a illustrates a dual-layer film of the invention.

A dual-layered disc, intra-oral dosage orally-dissolving film (ODF) of insulin, with dual colors: pink- and white-layer, was prepared according to the method of the invention, wherein the pink layer is the adhesive film (adhered to the buccal tissue) with insulin as an active ingredient, and the white layer is the blocking layer without insulin (see FIG. 2a). The white backing film layer (non-adhesive) provides unidirectional absorption of the drug to buccal tissue, i.e. block the drug from diffusion out in the opposition direction.

The obtained discs, named BNX-104-110511 contain 450 Insulin Units/disc, and demonstrate insulin stability for at least 3 month, as indicated in % insulin in ODF in the Table below:

| Temp. | % Insulin | Comments |
|---|---|---|
| t = 0° C. | 12.2 | |
| t = 1 mo at −20° C. | 12.2 | pass |
| t = 2 mo at −20° C. | 12.2 | pass |
| t = 3 mo at −20° C. | 12.2 | pass |
| t = 2 wk at 5° C. | 12.1 | pass |
| t = 1 mo at 5° C. | 12.1 | pass |
| t = 2 mo at 5° C. | 12.0 | pass |
| t = 3 mo at 5° C. | 11.8 | pass |
| t = 2 wk at 25° C. | 10.3 | oos |
| t = 3 mo at 25° C. | 8.90 | oos | oos: out of specifications

Insulin release from the above discs was analyzed:

The films were administered according to the following steps:
1. Cutting the wrapper along the indicated arrows, and separating the layers of the foil package;
2. Carefully placing the film inside the mouth with the pink side against the inside of the moistened cheek, and then pressing against the cheek for about 5 seconds;
3. Leaving the film in place until it dissolves (up to about 4 hours after placement).

Figure 2B:
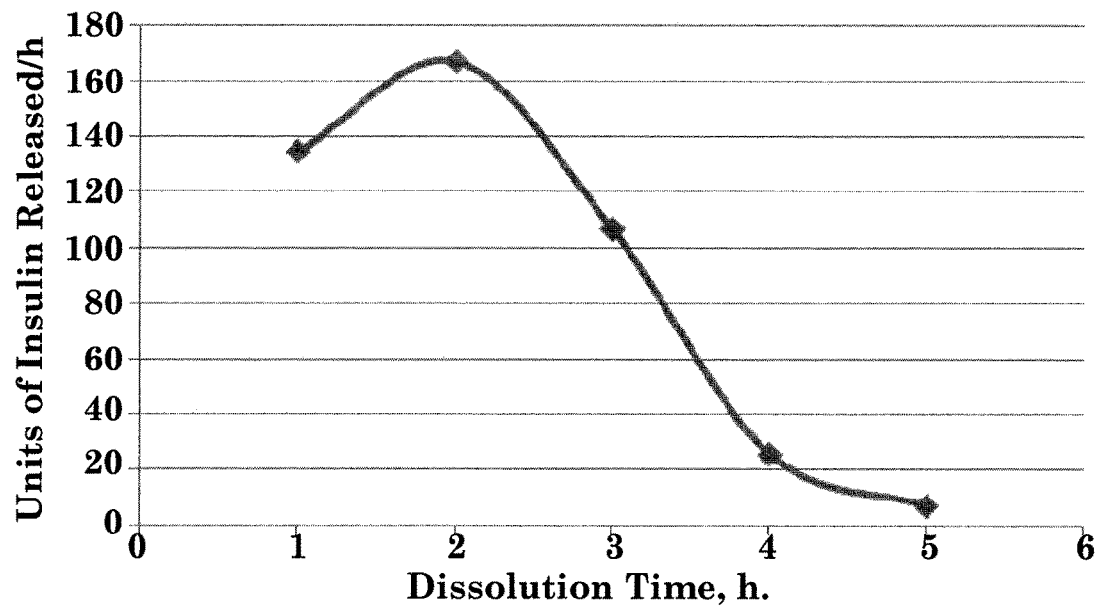
FIG. 2b is a graph summarizing insulin release data.
Figure 2C:
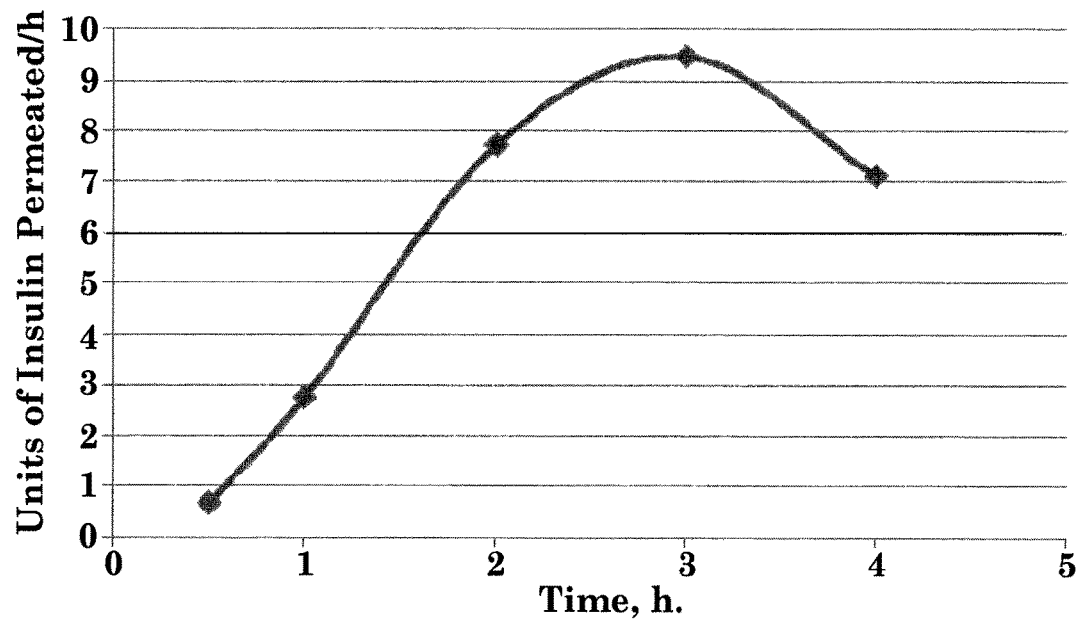
FIG. 2c is a graph summarizing insulin permeation data.

The results, as demonstrated in FIG. 2b and FIG. 2c, and as summarized in the Tables below, show that in FDL films, more than 50% of the insulin is released within 2 hours of administration, and that most of the insulin is released within 4 hours after disc application (FIG. 2b):

| Time (h) | units/h |
|---|---|
| 1 | 134.4 |
| 2 | 166.9 |
| 3 | 106.5 |
| 4 | 25.6 |
| 5 | 7.1 |

In addition, insulin permeation increases in time, reaching a maximum level within 3 hours (FIG. 2c) and the following Table:

| Time, h | Units/h |
|---|---|
| 0.5 | 0.68 |
| 1 | 2.76 |
| 2 | 7.72 |
| 3 | 9.46 |
| 4 | 7.11 |

Example 4

Formulations 104-101014

The following thin films were prepared according to Example 2 above:

| Ingredient | Function | Wet g | Dry g | Dry % |
|---|---|---|---|---|
| Ethanol | Casting solvent | 20.19 | | |
| Water | Casting solvent | 25.80 | | |
| Carbopol 971 NF | Film matrix polymer | 2.00 | 2.00 | 19.4% |
| Kollicoat IR | Film matrix polymer | 3.39 | 3.39 | 32.8% |
| Insulin | Active ingredient | 0.310 | 0.31 | 3.0% |
| Brij 35/Brij L23 | Permeation enhancer | 1.46 | 1.46 | 14.1% |
| Peppermint Oil USP | Flavoring agent | 0.33 | 0.33 | 3.2% |
| Art Strawberry Flavor | Flavoring agent | 0.16 | 0.16 | 1.6% |
| Versene NA | Chelating agent | 0.05 | 0.05 | 0.5% |
| PEG400 | Film plasticizer | 2.41 | 2.41 | 23.4% |
| Syncal GS | Sweetener | 0.21 | 0.21 | 2.0% |
| FD&C Red No. 40 | Colorant | 0.00 | | |
| Total | | 56.31 | 10.32 | |
| Ethanol | Casting solvent | 20.19 | | |
| Water | Casting solvent | 25.80 | | |
| Carbopol 971 NF | Film matrix polymer | 2.00 | 2.00 | 19.4% |
| Kollicoat IR | Film matrix polymer | 3.39 | 3.39 | 32.8% |
| Insulin | Active ingredient | 0.310 | 0.31 | 3.0% |
| Sodium glycocholate | Permeation enhancer | 1.46 | 1.46 | 14.1% |
| Peppermint Oil USP | Flavoring agent | 0.33 | 0.33 | 3.2% |
| Art Strawberry Flavor | Flavoring agent | 0.16 | 0.16 | 1.6% |
| Versene NA | Chelating agent | 0.05 | 0.05 | 0.5% |
| PEG400 | Film plasticizer | 2.41 | 2.41 | 23.4% |
| Syncal GS | Sweetener | 0.21 | 0.21 | 2.0% |
| FD&C Red No. 40 | Colorant | 0.00 | | |
| Total | | 56.31 | 10.32 | |

Each film is 2.3 cm×2.3 cm, weighs about 100 mg. Each film has adequate structural integrity and flexibility. Each film has 3% (theoretical value) insulin. HPLC assay showed that each film has 310 mg insulin.

To enable in vitro study of insulin release, the films were applied onto EpiOral tissues (MatTek) according to the Drug Absorption Protocol (ORL-202 & ORL-606), incorporated herein by reference. EpiOral tissues consist of normal, human-derived epithelial cells, which have been cultured to form multilayered, highly differentiated models of the human buccal phenotypes. EpiOral is a multilayered tissue consisting of an organized basal layer and multiple non-cornified layers analog to native human buccal tissue.

Example 5

Film Thickness

In order to evaluate the medically preferred thickness of the oral film, the following experiments have been performed:

As a first step, the effect of Carbopol on insulin release was tested by analyzing formulations containing 1% and 18% Carbopol. The results, as demonstrated in FIG. 3a, show that at high Carbopol concentrations (18%) the release rate of insulin is prolonged and optimal compared to low Carbopol (1%) formulations.

Subsequently, slow dissolving film (SDL) dosage forms were prepared in various thicknesses, each film containing:

| Ingredient | |
|---|---|
| Carbopol 971 | 19.4 |
| Kollicoat IR | 32.8 |

-continued

| Ingredient | |
|---|---|
| Brij 58 | 14.1 |
| Insulin | 3.0 |
| PEG 400 | 23.4 |
| Peppermint oil | 3.2 |
| Strawberry Flavor | 1.6 |
| Syncal GS | 2.0 |
| Sodium EDTA | 0.5 |
| Sodium Bicarbonate | 0.0 |

[% in the final (dried) composition]

Each film was tested for insulin release. The results are demonstrated in FIG. 3b, which show that insulin release profile was optimal at a film thickness of about 5.9 mil (~150 µm). In addition, the results show that in SDL films, most of the insulin is released from about 4 hours to about 12 hours, depending on the film thickness.

Example 6

In Vitro Buccal Tissue Permeation Experiments

In order to search for effective buccal permeation enhancers for transmucosal absorption of insulin, the following three permeation enhancers were tested:

Brij 58 (Croda Inc.), which is a non-ionic surfactant, also known as polyoxyethylene (20) cetyl ether;

Brij 35 (Croda Inc.), which is a non-ionic surfactant, also known as polyoxyethylene (35) lauryl ether (see Oh and Ritschel, Meth Find Exp Clin Pharmacol, 12(3): 205-212, 1990); and Sodium glycocholate (Spectrum Chemicals), which is a bile salt, (see Das et al, Pharm Dev Tech, 15(2):192-208, 2010).

Insulin solution (0.60 mg/mL) was prepared in phosphate buffer (pH 6.8) solution (PBS). The above mentioned potential permeation enhancers were dissolved in the insulin solution to make solutions with desired ratios given in the table below:

| Formulation ID | Insulin | Brij 35 | Brij 58 | Sodium Glycocholate |
|---|---|---|---|---|
| 0 (Control) | 100 | | | |
| 1 | 85 | | 15 | |
| 2 | 75 | | 25 | |
| 3 | 85 | 15 | | |
| 4 | 85 | | | 15 |

The in vitro permeation studies were performed using cultured human buccal tissue (EpiOral) (supplied by MatTek Corp., Ashland, Mass.) according to the protocol suggested by MatTek Corp. (Drug absorption protocol for use with EpiOral™ Tissue Model ORL-200 & ORL-606).

Briefly, experiments were conducted in 37° C. incubator with 0.9 mL of PBS in receptor. 3.5 mL of donor solutions (n=4 for each formulation) were placed in the donor compartments. Donor samples were collected from the receptor at time periods of 0.5, 1.0, 2.0, 3.0, 4.0 and 6.0 h, and were later assayed using HPLC.

Cumulative amounts of permeated insulin are summarized in the below Table (and in FIG. 4):

| | Cumulative µg | | | | |
|---|---|---|---|---|---|
| h | Control | Form 1 | Form 2 | Form 3 | Form 4 |
| 0.5 | 2.4 | 3.0 | 8.1 | 10.8 | 7.4 |
| 1 | 5.2 | 5.7 | 17.5 | 25.6 | 15.8 |
| 2 | 12.0 | 13.3 | 27.0 | 39.5 | 21.4 |
| 3 | 16.4 | 24.4 | 32.8 | 54.3 | 38.9 |
| 4 | 25.3 | 38.0 | 44.7 | 98.1 | 82.5 |
| 6 | 42.0 | 76.3 | 120.0 | 207.2 | 169.6 |
| % Permeated after 6 hours | 2.1% | 3.8% | 5.9% | 10.3% | 8.4% |

The results show that Brij 35 (polyoxyethylene lauryl ether) increases insulin release about 5 times more effectively when compared to the control (without a permeation enhancer). These results further show that Brij 35 demonstrates the highest permeation effectiveness for insulin among the 3 tested compounds, suggesting that it is the preferable permeation enhancer for transmucosal absorption of insulin.

In addition, these results show that after 6 hours the use of formulation 3 resulted in permeation of about 10% of insulin, suggesting that a single film may provide the patient with sufficient insulin for at least 12 hours, without the need to replace it.

Example 7

In Vitro Buccal Tissue Permeation Experiments

In order to determine the extent of transmucosal absorption of the Dual-Layer Insulin ODF Formulations of the invention, cultured buccal tissues were used (purchased from MatTek Corporation) as described in Example 6 above. Three formulation were tested as follows:

| Formulation ID | Insulin, mg/disc | Insulin, Units/disc | SLS, % | Menthol, % |
|---|---|---|---|---|
| 104-110511 | 16.5 mg | 450 | 4.5 | 4.0 |
| 104-110524 | 16.5 mg | 450 | 1.0 | 4.4 |
| 104-110526 | 16.5 mg | 450 | 0.0 | 4.7 |

Each disc is ¾-in in diameter.

The formulations containe:

| | 104-110511 | | | |
|---|---|---|---|---|
| Ingredient | Manufacturer | Wet g, Actual | Dry g | Dry % |
| Ethanol | | 15.31 | | |
| SLS | Croda | 0.52 | 0.52 | 4.3% |
| Menthol | Spectrum | 0.50 | 0.50 | 4.1% |
| Peppermint oil USP | AM Todd | 0.20 | 0.20 | 1.7% |
| Insulin | Biocon | 1.53 | 1.53 | 12.70% |
| Carbopol 971P | Noveon | 1.11 | 1.11 | 9.2% |
| Water | Lab | 32.41 | | |
| PEG400 | Dow | 2.15 | 2.15 | 17.8% |
| PolyOx N-10 | BASF | 5.83 | 5.83 | 48.4% |
| Syncal GS (Sacharrin) | PMC | 0.21 | 0.21 | 1.7% |
| Total | | 60.45 | 12.05 | |

| 104-110524 | | | | |
|---|---|---|---|---|
| Ingredient | Manufacturer | Wet g, Actual | Dry g | Dry % |
| Ethanol | | 15.39 | | |
| SLS | Croda | 0.13 | 0.13 | 1.1% |
| Menthol | Spectrum | 0.52 | 0.52 | 4.4% |
| Peppermint oil USP | AM Todd | 0.21 | 0.21 | 1.8% |
| Insulin | Biocon | 1.53 | 1.53 | 13.04% |
| Carbopol 971P | Noveon | 1.10 | 1.10 | 9.4% |
| Water | Lab | 32.40 | | |
| PEG400 | Dow | 2.15 | 2.15 | 18.3% |
| PolyOx N-10 | BASF | 5.85 | 5.85 | 49.9% |
| Syncal GS (Sacharrin) | PMC | 0.21 | 0.21 | 1.8% |
| FD&C Red No. 4 Al Lake | Colorcon | 0.03 | 0.03 | 0.3% |
| Total | | 60.45 | 11.73 | 100% |

| 104-110526 | | | | |
|---|---|---|---|---|
| Ingredient | Manufacturer | Wet g, Actual | Dry g | Dry % |
| Ethanol | | 15.47 | | |
| SLS | Croda | 0.00 | 0.00 | 0.0% |
| Menthol | Spectrum | 0.55 | 0.55 | 4.7% |
| Peppermint oil USP | AM Todd | 0.21 | 0.21 | 1.8% |
| Insulin | Biocon | 1.54 | 1.54 | 13.22% |
| Carbopol 971P | Noveon | 1.13 | 1.13 | 9.7% |
| Water | Lab | 32.65 | | |
| PEG400 | Dow | 2.17 | 2.17 | 18.6% |
| PolyOx N-10 | BASF | 5.84 | 5.84 | 50.1% |
| FD&C Red No. 4 Al Lake | Colorcon | 0.01 | 0.01 | 0.1% |
| Syncal GS (Sacharrin) | PMC | 0.20 | 0.20 | 1.7% |
| Total | | 60.45 | 11.65 | 100% |

Materials:

MatTek cultured human tissues; Product kit ORL-606. Three kits (each has 6 wells/tissues), one for each formulation, were used. For each formulation, six discs were used, each disc in one well.

All insulin ODF discs have two layers: pink layer is the bioadhesive layer containing insulin, and white layer is the no-drug blocking layer. The pink layers were in contact with the cultured human tissues for these experiments. 3.5 mL PBS pH 7.4 were added to the disc/tissue cell to completely cover the matrix during the 4 hours experimentation.

Experimental Method:

Experimental procedure outlined in MatTek's standard protocol was used, the subject of which is incorporated herein in its entirety. Phosphate buffer solution (PBS) at pH 7.4 is used in both donor (3.5 mL) and receiver (0.9 mL) compartments, all contained in the MatTek ORL-606 Kit.

The permeation assembly kit were contained in a 37° C. shaking incubator, agitated at low speed of 50 rpm. Receiver media were collected completed (i.e. all 0.9 mL) and replaced with fresh media PBS pH 7.4 at 0.5, 1, 2, 3, and 4 h, and later analyzed for insulin concentration using HPLC.

Results

After 4 hours of experimentation, extent of drug release in the donor compartment was:

| Form ID | 110511 | 110524 | 110526 |
|---|---|---|---|
| % Released | 49.2% | 43.2% | 32.7% |

Permeation results at the end of the experiment are:

| Formulation ID | 110511 | 110524 | 110626 |
|---|---|---|---|
| Insulin Units | 450 | 450 | 450 |
| SDS % | 4.3 | 1.0 | 0 |
| Menthol % at end of 4 h | 4.1 | 4.4 | 4.7 |
| mg released | 8.261 | 7.263 | 5.492 |
| mg permeated | 0.964 | 0.644 | 0.328 |
| % permeated | 11.7% | 8.9% | 6.0% |

Overall, Formulation 110511, which contains high percentage of both SDS and menthol, provides highest drug release and highest permeability (i.e. about 11%).

The rates of permeation during the 4 hours are presented in FIG. 5 and summarized in the following table:

| Sample | 110511 | 110524 | 110526 |
|---|---|---|---|
| | mcg | | |
| 0.5 | 12.6 | 10.1 | 6.2 |
| 1 | 51.1 | 55.4 | 31.9 |
| 2 | 286.1 | 172.6 | 121.4 |
| 3 | 350.5 | 206.9 | 94.5 |
| 4 | 263.4 | 199.5 | 74.4 |
| | Units Insulin | | |
| 0.5 | 0.34 | 0.27 | 0.17 |
| 1 | 1.38 | 1.50 | 0.86 |
| 2 | 7.72 | 4.66 | 3.28 |
| 3 | 9.46 | 5.59 | 2.55 |
| 4 | 7.11 | 5.39 | 2.01 |
| | Units Insulin/h | | |
| 0.5 | 0.68 | 0.55 | 0.33 |
| 1 | 2.76 | 2.99 | 1.72 |
| 2 | 7.72 | 4.66 | 3.28 |
| 3 | 9.46 | 5.59 | 2.55 |
| 4 | 7.11 | 5.39 | 2.01 |

These results demonstrate that insulin ODF formulations with 4.5% SDS and 4.5% Menthol provides excellent dissolution and permeation profiles.

Accordingly, the disintegrable oral films of the invention are useful as an insulin replacement therapy. The oral films may be used concurrently with other anti-diabetic medicaments, and in any dietary regimen. Thus, the present invention also relates to methods of treating diabetes by orally administering one or more of the orally dissolving films of the invention to a diabetic patient. The orally dissolving films are typically administered such that the insulin is delivered transbuccally in the mouth.

While the present invention has been described above in connection with the certain illustrative embodiments, it is to be understood that other similar embodiments may be used or modifications and additions may be made to the described embodiments for performing the same function of the present invention without deviating therefrom. Furthermore, all embodiments disclosed are not necessarily in the alternative, as various embodiments of the invention may be combined to provide the desired characteristics. Variations can be made by one having ordinary skill in the art without departing from the spirit and scope of the invention. Therefore, the present invention should not be limited to any single illustrative embodiment, but rather construed in breadth and scope in accordance with the recitation of the attached claims.

The invention claimed is:

1. A dual-layer flexible thin film dosage form for buccal delivery of insulin or analogs thereof, comprising a first polymeric layer and a second polymeric layer, wherein an active agent selected from the group consisting of insulin, insulin analogs, and mixtures thereof, is located only in the first polymeric layer, and not in the second polymeric layer, in an amount of 0.5-10 wt %, said film further comprising:
 about 10 to about 15 wt % polyoxyethylene lauryl ether;
 about 1 to about 10 wt % flavoring agent(s);
 about 0.01 to about 1 wt % EDTA;
 about 20 to about 25 wt % PEG 400; and
 about 40 to about 60 wt % polyethylene glycol-polyvinyl alcohol copolymers and polymers of acrylic acid crosslinked with polyalkenyl ethers or divinyl glycol.

2. The thin film dosage form of claim 1, wherein each one of the first and second layers has a distinct color.

3. The thin film dosage form of claim 1, wherein the first layer is laminated.

4. The thin film dosage form of claim 1, wherein the film dosage form additionally contains at least one further pharmaceutically active substance which is not insulin or an analog thereof.

5. The thin film dosage form of claim 1, wherein the film dosage form is suitable for treating diabetic patients.

6. A kit suitable for treating diabetes, which comprises the thin film dosage form of claim 1.

7. The thin film dosage form of claim 1, wherein said insulin or insulin analogue is a short-acting form of insulin.

* * * * *